United States Patent [19]

Stoy et al.

[11] Patent Number: 5,218,039
[45] Date of Patent: Jun. 8, 1993

[54] PAN EMULSION

[75] Inventors: Vladimir Stoy; Jan Lovy, both of Princeton, N.J.

[73] Assignee: Kingston Technologies, Inc., Dayton, N.J.

[21] Appl. No.: 43,327

[22] Filed: Apr. 28, 1987

[51] Int. Cl.$^5$ ............................................. C08L 9/02
[52] U.S. Cl. ............................. 524/566; 524/317; 524/379; 524/388; 524/565; 524/827
[58] Field of Search ................ 524/566, 827, 565

[56] References Cited

U.S. PATENT DOCUMENTS

| | | | |
|---|---|---|---|
| 2,734,041 | 2/1956 | Jones et al. | 524/566 |
| 2,812,317 | 11/1957 | Barrett | 524/566 |
| 3,615,791 | 10/1971 | Thomas et al. | 524/566 |
| 4,107,121 | 8/1978 | Stoy | 524/566 |
| 4,272,422 | 6/1981 | Tanaka | 524/566 |

FOREIGN PATENT DOCUMENTS 0659583 4/1979 U.S.S.R. ............................. 524/566

Primary Examiner—Joseph L. Schofer
Assistant Examiner—J. M. Reddick
Attorney, Agent, or Firm—Kenneth P. Glynn; Richard C. Woodbridge

[57] ABSTRACT

Stable emulsions and dispersions of both the water-in-oil and oil-in-water types are prepared by subjecting mixtures of the two phases to shear stress in the presence of nitrile group-containing copolymers capable of forming hydrogels containing at least 90% by weight of water at room temperature.

12 Claims, 1 Drawing Sheet

PAN EMULSION

This invention relates to stable emulsions and dispersions containing a polar aqueous phase, a water-insoluble non-polar phase, and an acrylonitrile copolymer emulsifying or dispersing agent, and to a method of making such emulsions and dispersions. By "stable" is meant emulsions and dispersions which do not exhibit phase separation when maintained at room temperature for prolonged periods, say 2 days or more.

BACKGROUND OF THE INVENTION

Acrylonitrile copolymers capable of forming hydrogels containing at least 90% by weight of water at room temperature are well known in the art. Preferably, the total number of nitrile groups

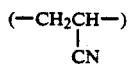

in such copolymers is between 5 and 75 percent (more preferably between 10 and 50 percent) of all substituent groups present, and at least 1/5 of such nitrile groups (preferably at least ½ ) are arranged in sequences containing at least 5 adjacent nitrile groups; they may be considered either graft or block copolymers, preferably the latter.

One group of such acrylonitrile-based hydrogels is linear polymers having a hydrocarbon backbone to which are bonded nitrile groups along with other substituent groups such as carboxyl, carboxylate salt, carboxylic ester, and amide and imide groups. They may or may not be covalently cross-linked. For the most part such copolymers are made by partial hydrolysis of polyacrylonitrile (PAN) under appropriate conditions; the hydrolysis can be catalyzed by either acid or base. They are described, for example, in Stoy U.S. Pat. No. 4,107,121, which is incorporated herein by reference.

Another group of such acrylonitrile-based hydrogels is polysaccharides, e.g., starch, grafted with polyacrylonitrile segments (SPAN), which are then hydrolyzed with base to acrylic acid or acrylamide segments to form the hydrogels. Under certain controlled hydrolysis conditions, however, the hydrolyzed copolymer contains residual nitrile groups in sequences of 5 or more.

The acrylonitrile copolymer emulsifying and dispersing agents of the present invention are those acrylonitrile copolymers which are capable of forming hydrogels containing at least 90% by weight of water at room temperature, i.e. hydrogels which retain their form and shape without liquid flow when allowed to stand at room temperature. Such copolymers are, as a rule, not crosslinked by covalent bonds. The three-dimensional network in such hydrogels is formed by interactions between the nitrile group

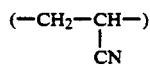

sequences which form crystalline clusters. The clusters are crystalline domains whose structure resembles closely that of PAN itself (for instance, the essential features typical for PAN can be detected in X-ray diffraction patterns of such hydrogels). The hydrogels can also be formed by acrylonitrile copolymers crosslinked covalently to supplement the physical network of the type indicated above, although the latter is dominant with respect to the important physical properties.

The emulsions and dispersions of the present invention contain an aqueous polar phase and a water-insoluble nonpolar phase. The aqueous phase may contain in addition to water various water-soluble polar materials such as alcohol, glycols, acids and/or salts thereof, while the non-polar phase may contain a variety of water-insoluble solids or water-insoluble non-polar liquids with or without water-insoluble solids dissolved therein. Examples of important emulsions and dispersions which can be made in accordance with the present invention and their uses are milk and other food products; food substitutes and additives; latices, both synthetic and natural, e.g. latex paints and adhesives; creams, lotions, and ointments in cosmetics and health care; cooling and lubricating emulsions, hydraulic fluids; emulsion polymerization medium for numerous important monomers; liquid membrane systems, drug delivery systems, implantable tissue augmentation and many others. Recently, one special group of emulsions (liposomes) is being developed for targeted and controlled drug delivery.

SUMMARY OF THE INVENTION

It has now been found that stable emulsions and dispersions containing a polar aqueous phase and a water-insoluble nonpolar phase can be made by mixing said phases with a copolymer of a nitrile group-containing monomer, e.g., acrylonitrile, capable of forming a hydrogel containing at least 90% by weight of water at room temperature, and subjecting said mixture to shear stress. Preferred are emulsions and dispersions made with acrylonitrile copolymers capable of forming hydrogels containing at least 95% water; particularly preferred are those copolymers capable of forming hydrogels containing at least 98% water. Also preferred are emulsions and dispersions made with such copolymers containing no covalent crosslinkages, which copolymers at temperatures above about 50° C. are soluble in water to form liquid solutions, not gels. Such emulsions and dispersions are highly thixotropic, with viscosity strongly dependent upon temperature, and stable both at high and low temperatures.

The amount or concentration of acrylonitrile copolymer employed can be varied over a wide range, as in the case of conventional emulsifiers. As little as 0.05% by weight based on the aqueous phase is effective in some cases, while amounts up to 5% by weight or even more can be used in certain cases; typically, the copolymer concentration ranges from 0.1 to 2% by weight. The amount desired in any particular case can readily be determined by simple experiment. The amount of the nonpolar phase preferably is no greater than about 50% by weight based on the total composition weight in order to form an oil-in-water emulsion.

In the drawing,

The FIGURE is a graphical representation of the change in viscosity in centipoises with change in shear stress in RPM in a Brookfield Viscometer at 25° C. of one emulsion of the present invention.

Particularly stable are emulsions and dispersions formed in the presence of copolymers containing, in addition to the acrylonitrile units, acrylic acid salt units.

The emulsions and dispersions according to the invention are stable under a broad range of conditions and can be broken by evaporation of water or by a change of conditions which substantially changes the swelling capacity of the copolymer used (such as change of pH, salt concentration, addition of polymer-precipitating organic solvents, etc.).

Although oil-in-water emulsions and dispersions are the type most useful, water-in-oil emulsions and dispersions are also possible, and both types can coexist in one system.

In addition to the three basic components (i.e. polar aqueous phase, water-insoluble nonpolar phase and acrylonitrile copolymer), the emulsions and dispersions according to the invention may contain any additives which do not destabilize them, such as pigments, ultraviolet absorbents, fillers, fragrances, dyes, auxiliary emulsifiers, water-miscible organic additives (such as alcohols, glycerine, 1,2-propanediol, polyethyleneglycol, saccharides and polysaccharides, proteins and components or fragments thereof), drugs and biologically-active compounds, preservatives, salts, amino acids, surfactants, radiopaque additives, water-soluble polymers or thickening agents to improve the properties and utility of such emulsions. Depending upon their characteristics the additives may form part of the aqueous phase or of the water-insoluble non-polar phase.

DESCRIPTION OF THE PREFERRED EMBODIMENTS

Figure 1:
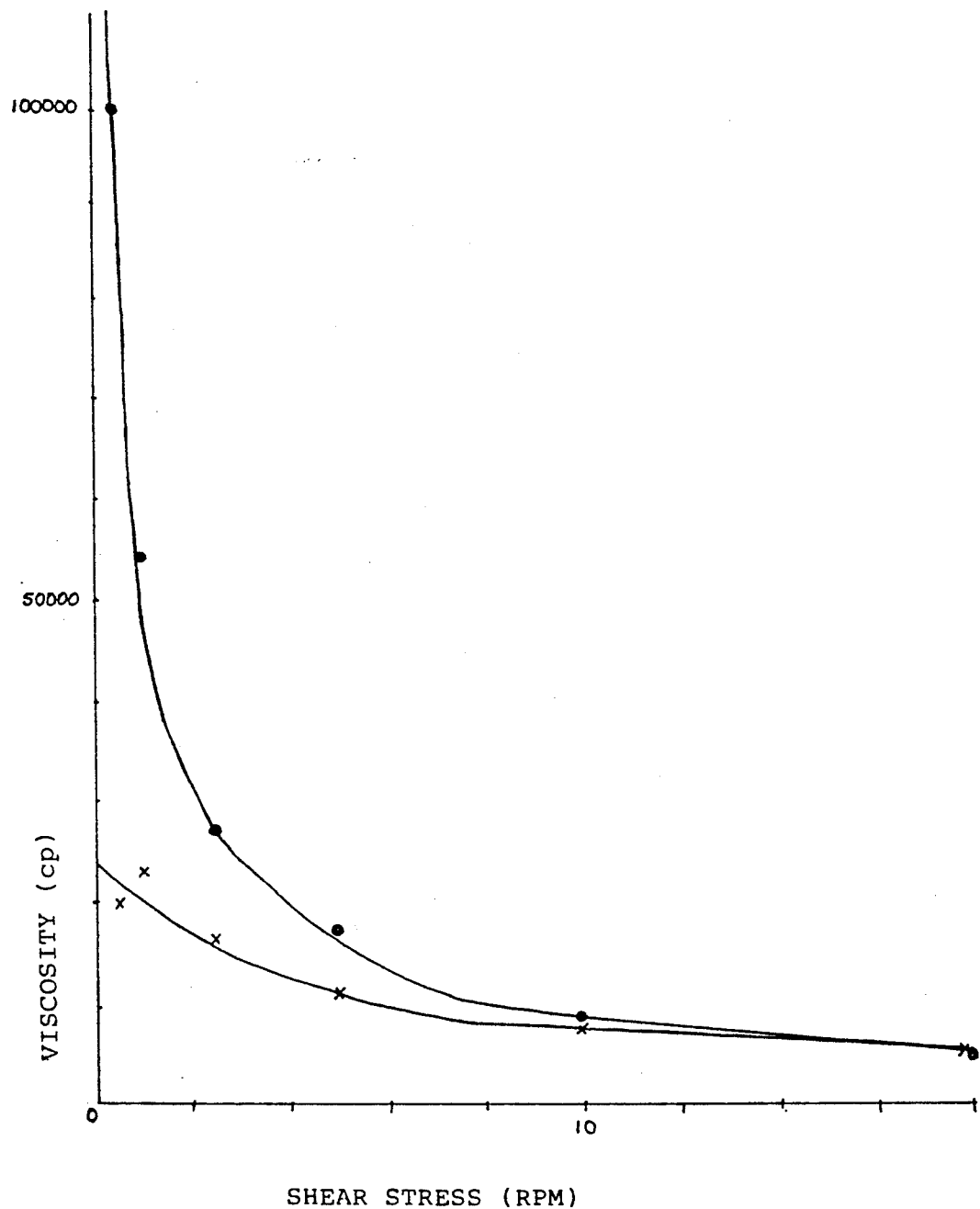

We have found that a non-polar liquid, such as mineral oil, octadecanol or corn oil can be emulsified in water containing an acrylonitrile copolymer as defined above if mixed under high shear, such as in a blender or even a food processor. The emulsions thus formed are stable under a broad range of conditions and have certain unusual properties described below.

The most unexpected property is the emulsion stability itself. The acrylonitrile copolymers are composed of sequences of acrylonitrile units and sequences of a hydrophilic acrylic acid derivative, such as acrylate salt, acrylamide, acrylhydroxamic acid, acrylhydrazide, an hydrophilic acrylic ester, and the like. The acrylonitrile sequences are highly polar, as witnessed, for instance, by the solubility parameter of polyacrylonitrile itself, which has a value of 15.4. Polyacrylonitrile (or corresponding sequences in the hydrogel) cannot be considered a non-polar or lipophilic moiety by any stretch of the imagination. The hydrophilic sequences of the copolymer are also highly polar, and a corresponding homopolymer would be water-soluble. Therefore, the non-polar moiety conventionally deemed essential for an effective emulsifier is missing completely. In addition to that, a hydrogel is both oil- and water-insoluble by definition, forming discrete particles with highly hydrated surfaces. Therefore, the copolymers are lacking the most important and basic characteristics of usual emulsifiers. In spite of that, they appear to be very efficient emulsifiers and dispersing agents, yielding—even in absence of other emulsifying agents—stable emulsions and dispersions.

Without limiting the scope of this invention, our tentative hypothesis of emulsifying or dispersing efficiency of the acrylonitrile copolymers assumes that the acrylonitrile sequences are organized in a planar conformation with respect to the dipolar nitrile groups, which are engaged in complementary interaction with nitrile groups from different sequences with opposite orientation. Therefore, each crystalline cluster is composed of several layers of nitrile groups in planar conformation. In this way the polar forces of the nitriles are mutually compensated and each cluster behaves as a non-polar moiety, exposing only the paraffinic backbones to the environment. Because such organization is hindered by any covalent crosslinking, the non-crosslinked copolymers show higher emulsification efficiency. Because the crystalline clusters are not permanently bonded, the high shear forces during the mixing can help their rearrangement necessary for their sorption on the water-oil interface.

The nitrile groups should be arranged in sequences of at least 5 in order to form such clusters. The total number of nitrile groups in the copolymer required for effective cluster formation will vary depending on the length of the sequences—as sequence length increases, the total number of nitrile groups needed decreases. In general, the total number of nitrile groups is preferably between 5 and 75% of all substituent groups present and more preferably between 10 and 50%; at nitrile contents above 75%, the clusters become too large and rigid to achieve proper orientation at the oil-water interface.

The particular method used to prepare such copolymers is unimportant as long as the above-described nitrile sequences are formed. Examples of suitable methods include copolymerizing acrylonitrile with hydrophilic polymers, grafting acrylonitrile onto a hydrophilic polymer and then polymerizing the acrylonitrile, or grafting a hydrophilic monomer onto polyacrylonitrile and then polymerizing it. Other suitable methods include chemically modifying polyacrylonitrile by partial hydrolysis to form the copolymer or chemically coupling a polyacrylonitrile precursor to a hydrophilic polymer.

The clusters probably survive even if a copolymer hydrogel as a whole is melted, by which is meant melting of the crystalline PAN domains, which causes the hydrogel to lose its coherent three-dimensional structure. This could explain the stability of the emulsions at high temperatures when viscosity is low (in other words, the system is a true stable emulsion or dispersion rather than a dispersion in which phase separation is hindered by the high viscosity of the continuous phase).

The copolymers having low concentration of the nitrile clusters such that a hydrogel formed from it can melt in water upon heating appear to be more efficient emulsifiers and dispersing agents than those with higher concentration of nitrile groups and, therefore, lower hydrogel water content and higher melting point. In other words, the emulsifying or dispersing efficiency (measured, for instance, by the concentration of the polymer necessary to achieve emulsion stability) increases with increasing water content in the hydrogel formed by the copolymer. This appears to support our hypothesis, because the less organized and more mobile clusters can take the thermodynamically advantageous position on oil-water interface with ease, while the stronger clusters need more time and energy for similar rearrangement. Our hypothesis is supported by the fact that emulsions and dispersions made with copolymers capable of forming less swellable hydrogels need higher shear and longer mixing time to achieve the same stability as those forming weaker hydrogels with higher water content.

The viscosity of emulsions and dispersions according to our invention is significantly higher than the viscosity of any liquid component. In addition, they are distinctly thixotropic, i.e. their viscosity is much higher at rest than when a shear stress is applied. This indicates that the polymer chains are sorbed on the oil-water interface on one hand, and in mutual interaction on the other. We believe that this is so due to the fact that several PAN sequences are on each polymer chain so that they can engage in the two types of interactions simultaneously. As a consequence, our emulsions and dispersions appear to be structured in more a complicated manner than those with other emulsifiers or dispersing agents, resembling perhaps liposomes in some respects.

Since the crystalline domains (which are presumably adsorbed in the oil or water-insoluble non-polar phase) and hydrophilic domains cannot be physically separated, water is probably present both as continuous phase (as in classical emulsions) and as discontinuous phase (i.e. entrapped in the water-insoluble non-polar phase via hydrated domains in close vicinity of the crystalline domains).

The high viscosity and thixotropy of our emulsions and dispersions is beneficial in many applications. For instance, a skin cream based on our emulsions is very easy to spread into a very thin layer, but does not run or drip in thick layer, so that it combines the properties of a cream and a lotion in an optimum manner.

Another example of the benefits can be a latex paint based on our emulsion or dispersion which has a gel-like consistency while in the can (so that the pigments or other particulate components do not sediment), but can be sprayed, applied by a brush or a roller as a paint of low viscosity. As an additional benefit, our paint does not drip, run, or streak. Also, it is stable during freeze/thaw cycling.

Still another example of the benefits can be the use of our emulsion or dispersion in a food or as a food additive. For instance, the emulsion of water, vegetable oil and acrylonitrile copolymer can have the consistency, look and rheological properties of mayonnaise. The small amount of acrylonitrile copolymer plays the roles of emulsifier, thickening agent and thixotropic additive simultaneously, thus replacing an array of compounds in the natural product. Because the acrylonitrile copolymer is a non-toxic, inert additive without any caloric content or nutritional function, it could be a suitable dietary alternative for the natural product. In addition, the emulsions formed with the acrylonitrile copolymer are more stable, and can be boiled, heat-sterilized and stored for extended periods of time.

Another valuable property of the emulsions and dispersions according to the invention is their ability to melt reversibly. The viscosity of the emulsion or dispersion decreases with increasing temperature more steeply than the viscosity of the continuous (aqueous) phase, due to melting of the crystalline PAN domains. This is valuable particularly in the case of highly viscous, gelatinous emulsions and dispersions, which can be melted and cast into any desirable shape. They can also be diluted with water or compounded with additives in the molten state without applying shear.

Still another unique and useful property is the destabilization of the emulsion or dispersion by the evaporation of water. As the water evaporates, the emulsion or dispersion breaks into a continuous non-polar phase. This happens first on the surface, whereupon the thin surface layer of non-polar material formed slows down the further evaporation, so that the emulsion or dispersion is stable for a long time at ambient (room temperature) conditions. This property can be used for the formulation of varnishes, polishes, water-proofing of wood or leather, and similar applications. Although the emulsion or dispersion can be readily diluted with water, washed, etc., once applied in a thin layer on the substrate, it is rapidly converted into a smooth and continuous layer of, e.g. wax, rosin, crosslinking oil or rubber.

Another potentially important property is the insolubility of highly thixotropic gelatinous emulsions and dispersions in water below their melting temperature (i.e. the melting temperature of the crystalline PAN domains). Such emulsions and dispersions closely resemble fat in tissue, and can be used for tissue augmentation in dermatology and cosmetic surgery. Because of its high thixotropy, the emulsion or dispersion can be applied subdermally, intradermally or intramuscularly, and will penetrate into interstices between the cells. Once at rest, it becomes insoluble and fills the space just as natural fat cells would. Because the solidification is a purely physical process without any chemical reaction, change in osmolarity in surrounding tissue, or release of solvents, the application is an atraumatic event. The "synthetic fat" is stable (compared to, e.g. collagen), but can be molded by temporarily heating it above the melting temperature of the crystalline PAN domains using, e.g. ultrasound; removal of the heat source causes the hydrogel to re-solidify. The emulsion or dispersion can also be combined with or contain water-soluble (e.g. antibiotics) or water-insoluble drugs (e.g. steroids), so that the subdermally injected emulsion or dispersion can be used for a protracted drug delivery.

The invention can be illustrated by the following non-limiting examples:

EXAMPLE 1

Polyacrylonitrile of molecular weight 350,000 was dissolved in a mixture of 71% nitric acid and 98% sulfuric acid (mixed in a weight ratio of 9:1) to form a viscous solution containing 5 wt % of the polymer. The solution was kept at ambient temperature for several days until about 90% of the nitrile groups were hydrolyzed to form a PAN copolymer. The reaction was then stopped by pouring the solution into excess cold water, so that the solution coagulated into a soft, clear PAN copolymer gel containing about 95% of water after washing. The washed copolymer was dried and ground to a fine powder. The copolymer contained about 12% of nitrile groups, more than 80% of amide groups, and the balance of carboxylic acid and imide groups. X-ray diffraction indicated continuous polyacrylonitrile sequences.

7.5 grams of the powdered copolymer was suspended in 990 grams of cold water. The suspension was then heated to boiling until the powder dissolved. The solution thus formed was cooled to ambient temperature to form a very soft, clear integral gel. The gel could be repeatedly melted or dissolved by heating and gelled or solidified by cooling.

500 grams of pure corn oil was added to the above gel and the mixture was mixed in a high-speed blender at ambient temperature for several minutes. A stable, creamy emulsion was formed.

If heated to 100° C., the emulsion's viscosity decreased but no phase separation was observed even after extended heating (several days). The emulsion gelled upon cooling, its viscosity being substantially higher than before or during the heating. The emulsion was also stable under the effect of ultrasound. If pushed through the needle of a syringe, the emulsion flowed freely but regelled immediately after it exited the needle, thus indicating high thixotropy.

The emulsion was readily dilutable with water in the molten state. It was immiscible with water or saline in the gelled state.

EXAMPLE 2

One (1) gram of the copolymer from Example 1 was dispersed in 400 grams of water and heated until it dissolved. Cooling of the solution did not cause it to gel visibly as in Example 1, although the solution viscosity increased significantly, indicating the presence of a hydrogel.

100 grams of octadecyl alcohol was added and the solution was stirred in a high-speed blender for about 20 seconds. A stable emulsion was formed. The emulsion withstood heating without phase separation. However, it did visibly gel upon cooling.

The emulsion was diluted with water without loss of stability. Also the addition of 10% glycerol, ethylalcohol, or isopropanol did not decrease the emulsion stability.

The emulsion served as a base for cosmetic lotion.

EXAMPLE 3

Hydrolysis of polyacrylonitrile (MW=150,000) by 3% aqueous sodium hydroxide at ambient temperature yielded a copolymer containing amide and carboxylic acid units. The copolymer was treated for several hours with 5% sulfuric acid, then washed with water to pH about 6. The pellets of copolymer, containing less than 50% water, were soaked in a 5% solution of ammonium bicarbonate to open cyclic imide groups and neutralize carboxyl groups. The copolymer thus formed contained about 70 mole % of nitrile units, about 20% of ammonium salt units and about 10% of amide units. $^{13}$C NMR spectrum showed that the nitrile groups were organized in continuous sequences. The copolymer was soluble in aqueous sodium thiocyanate solutions, indicating the absence of covalent cross-linking. If coagulated from such solution by pouring it into excess saline it formed a hydrogel containing about 91% by weight of isotonic saline.

The copolymer in pellet form was thoroughly washed, dried and ground to a fine powder. Ten (10) grams of the powdered copolymer was dispersed in 1 liter of water. The suspension was refluxed for several hours, then cooled down to ambient temperature to form a slurry. 200 grams of the pasty slurry was mixed with 125 grams of glyceryl oleate in a high-speed blender for about 20 minutes. A highly viscous, pasty emulsion was formed, which was heated in a closed bottle to 90° C. for about 2 hours. Upon cooling, a highly thixotropic emulsion was formed.

The emulsion was added to 500 ml of 0.9% NaCl solution in a blender running at a moderate speed. The emulsion particles formed a stable dispersion in the continuous aqueous phase, where the "oil phase" contained a substantial fraction of water. This "double emulsion" resembled a dispersion of liposomes in a number of important respects and could also perform similar functions.

EXAMPLE 4

A copolymer of acrylonitrile with 7% of methylacrylate (MW=90,000) was hydrolyzed by 5% KOH at ambient temperature for about 100 hours, until its swelling capacity in the form of a hydrogel reached about 500 to 600 grams of water per 1 gram of dry polymer in equilibrium at ambient temperature. The copolymer contained less than 20% (mol.) of nitrile units organized in blocks of molecular weight about 250 or more, the balance being formed by acid salt and amide groups in a molar of ratio about 2:1. The copolymer had high absorption in the UV region around 380 nanometers.

The copolymer was processed as described in Example 3 to form a fine powder. Five (5) grams of copolymer was then dispersed in 1 liter of water at ambient temperature and stirred for about 1 hour until a fine, viscous slurry was obtained. 500 grams of mineral oil and 150 grams of glycerol were added to the slurry, and the mixture was blended in a high-speed blender for several minutes. Highly viscous, thixotropic emulsion was formed which could be reversibly melted by heating above about 50° C. to form a creamy liquid.

Cooling the emulsion caused it to form a gel. The emulsion was stable in both the molten and gelled state, and was considerably stable even if part of the water evaporated. Evaporation of water caused formation of a rather compact gel composed of glycerol-swollen polymer and the oil. In contact with water, the gelled emulsion swelled back to its original consistency. The emulsion was stable also at freezing temperatures, and could be sterilized by autoclaving.

EXAMPLE 5

Ten (10) grams of the copolymer from Example 4, 600 grams of water and 400 grams of a 2% solution of androstanazone in cottonseed oil were mixed in a high speed blender until a cheesy, highly thixotropic emulsion was formed. The composition could be injected subcutaneously through a hypodermic needle, forming a long term deposit of the anabolic steroid.

EXAMPLE 6

To compare the effect of an acrylonitrile copolymer on the stability and viscosity of latex emulsions, the following two emulsions were prepared (Samples A and B).

Sample A

Commercial interior white latex paint having the following composition:

| | |
|---|---|
| TiO$_2$ (Type 2) | 10.1% |
| CaCO$_3$ | 6.2% |
| Silica/silicates | 26.7% |
| Vinylacrylic resin | 6.9% |
| Additives | 1.3% |
| Water and glycerols | 48.8% |

Sample B 1 kg of Sample A latex was mixed with 7 grams of the copolymer from Example 4 and 50 grams of isopropyl alcohol (to help to break bubbles). The mixture was homogenized in a high-speed blender for 10 minutes to form a highly thixotropic, creamy semi-gel-looking liquid. The aqueous phase of the original paint now contained highly swollen hydrogel microparticles.

The viscosities of Sample A and Sample B were measured using a Brookfield viscometer at 25° C. at various shear rates.

The drawing shows the dependence of viscosity ($\eta$) (in cP) vs. shear rate ($\gamma$) (in RPM) for Sample A (Curve 1) and Sample B (Curve 2).

FIG. 1 demonstrates that the hydrogel increased emulsion viscosity at shear rates up to about 10 RPM.

The modified latex paint of Sample B could be as easily spread by brush or roller as the original paint, but formed a better quality surface if applied in a thick layer. There was no paint loss during its application because it did not drip from the brush or roller. If applied on vertical surface, it achieved the same thickness after one coating as that achieved after applying two or three coatings of the original paint.

While the original paint started to sediment after several hours, the copolymer modified paint stayed in the can without any sedimentation for several months. The hydrogel additive also increased the emulsion stability during freeze-thaw cycling.

EXAMPLE 7

0.5 gram of the copolymer from Example 4 was mixed with 500 ml of water and 700 g of glyceryl stearate in a high-speed blender for about 20 minutes. The creamy emulsion thus formed was not dilutable by water but was dilutable by oil, indicating a water-in-oil emulsion.

100 g of this emulsion was mixed with a dispersion of 0.1 gram of the copolymer from Example 4 in 200 ml of water. The emulsion reverted into an oil-in-water type, while the oil phase retained a substantial amount of the polymer and water in it, thus forming a water-in-oil-in-water emulsion.

EXAMPLE 8

20 grams of polyisobutylene (MW=4,000) was dissolved in 20 grams of chloroform and 60 grams of toluene. The solution was blended into a slurry of 1.2 grams of the polymer from Example 4 in 200 ml of water in a high speed blender. The emulsion thus formed was stable in a closed container. If spread in a thin layer, water evaporated and the emulsion converted into a thin continuous layer of the polyisobutylene solution. The emulsion was useful as a water-dilutable but water-resistant adhesive.

EXAMPLE 9

12.0 grams of wheat starch (Hercules Star Bake grade) were dispersed in 250 grams of distilled water, stirred at 50° C. for 1 hour until swollen, and then cooled to ambient temperature. 17.5 grams of distilled acrylonitrile and 4.1 ml of an initiator solution (0.1N ceric ammonium nitrate in 1N nitric acid) were added to the aqueous starch dispersion under a nitrogen blanket. The mixture was homogenized and left overnight at 25° C. to allow the acrylonitrile to graft onto the starch. The grafted starch (S-PAN) was then extracted with hot water to remove unreacted starch and with DMF to remove any acrylonitrile homopolymer. The purified S-PAN contained about 57.5% by weight of grafted PAN (determined from nitrogen content). The average molecular weight of the PAN graft was estimated to be between about 250,000 and 500,000 daltons.

The S-PAN was washed in water to remove DMF and then centrifuged to remove excess water. Next, it was dispersed in NaOH solution (3% by weight) to hydrolyze the acrylonitrile units. Hydrolysis was carried out at 22° C. and monitored by measuring the concentration of NaOH in the liquid phase using titration. When 50% of the nitrile groups had been converted to carboxyl groups, hydrolysis was terminated by neutralizing residual NaOH with dilute sulfuric acid (pH=3.5). The copolymer was then centrifuged and washed in water, neutralized with a slight excess of ammonium bicarbonate, and finally dried at 60° C.

The resulting copolymer contained about 40 wt. % of starch and about 60 wt. % of graft. The graft consisted of about 50 mol % ammonium acrylate, 25 mol % acrylamide, and 25 mol % acrylonitrile. NMR analysis indicated that the concentration of nitrile groups contained in sequences of at least 5 or more was at least 10 mol % based on the graft fraction. This copolymer is further referred to as Sample A.

For comparative purposes, S-PAN was also hydrolyzed at 80° C. using 8.5% NaOH to hydrolyze all nitrile groups as described, e.g., in Weaver et al., *J. Appl. Polym. Sci.* 15:3015 (1971). This fully hydrolyzed S-PAN, now referred to as Sample B, was processed in the same fashion as Sample A.

Five grams of Sample A were dispersed in 995 grams of water, allowed to swell for 2 hours at ambient temperature, and then run through a colloid mill to get a slurry of fine uniform swollen particles. The slurry behaved as a viscous, thixotropic solution (Slurry A). Slurry B was prepared in an identical manner. Next, 50 grams of pure corn oil was mixed with 100 grams of Slurry A in a high speed blender, and the emulsion thus formed (Emulsion A) passed through the colloid mill. It was then stored in a closed bottle. Emulsion B was then prepared from Slurry B in an identical manner. Although Slurry A and Slurry B looked rather similar, Emulsions A and B showed marked differences:

a. Emulsion A had a higher viscosity than Slurry A, with pronounced thixotropic character. Emulsion B had a viscosity similar to that of Slurry B.

b. If left still at an ambient temperature in a closed container, Emulsion A was stable over a period of several months. Emulsion B showed signs of separation after several hours, and in two days the major part of oil was separated in continuous layers. This shows that Emulsion A is a true emulsion while Emulsion B is merely a dispersion of oil phase in viscous aqueous phase, so that phase separation is merely slowed down.

c. When heated to 90° C. in a closed bottle, Emulsion A melted into a thin, milk-like liquid, but no phase separation could be observed even after several hours. When cooled down, the emulsion regained its original gel consistency. When Emulsion B was heated, its viscosity was reduced just slightly and phase separation accelerated. After 1 hour Emulsion B was broken into two immiscible layers which stayed separated after cooling. This confirms the observation made above that Emulsion B is not thermodynamically stable.

Because Sample A and Sample B differed only in the presence or absence of nitrile sequences, this example illustrates the essential role of the nitrile sequences for stability of the emulsions according to our invention.

What is claimed is:

1. A stable emulsion or dispersion comprising
   a polar aqueous phase,
   a water-insoluble non-polar phase, and
   an emulsifying or dispersing agent comprising a copolymer of a nitrile group-containing monomer capable of forming a hydrogel containing at least 90% water by weight at room temperature.

2. The emulsion or dispersion of claim 1 in which said copolymer is capable of forming a hydrogel containing at least 95% water.

3. The emulsion or dispersion of claim 1 in which said copolymer is capable of forming a hydrogel containing at least 98% water.

4. The emulsion or dispersion of claim 1 in which said copolymer is free from covalent crosslinkages.

5. The emulsion or dispersion of claim 1 in which said copolymer is a product of partial hydrolysis of polyacrylonitrile.

6. The emulsion or dispersion of claim 5 in which said hydrolysis is acid hydrolysis.

7. The emulsion or dispersion of claim 5 in which said hydrolysis is alkaline hydrolysis.

8. The emulsion or dispersion of claim 1 further comprising at least one additive soluble in said polar phase or said non-polar phase.

9. The emulsion or dispersion of claim 1 wherein said additive comprises a vitamin, drug, insecticide, pesticide, or ultraviolet absorbent.

10. The emulsion or dispersion of claim 1 wherein the amount of said copolymer is at least 0.05% 5% by weight based on said aqueous phase.

11. The emulsion or dispersion of claim 1 wherein the amount of said copolymer is between 0.05 and by weight based on said aqueous phase.

12. The emulsion or dispersion of claim 1 wherein the amount of said copolymer is between 0.1 and by weight based on said aqueous phase.

* * * * *